(12) United States Patent
Gravesen et al.

(10) Patent No.: US 10,702,632 B2
(45) Date of Patent: Jul. 7, 2020

(54) MEDICAL TUBE ARTICLE

(71) Applicant: UNOMEDICAL A/S, Lejre (DK)

(72) Inventors: Per Otto Børresen Gravesen, Tikøb (DK); Torsten Winther, Chester (GB); Karsten Aakerlund, Hørsholm (DK)

(73) Assignee: UNOMEDICAL A/S, Birkerød (DK)

( * ) Notice: Subject to any disclaimer, the term of this patent is extended or adjusted under 35 U.S.C. 154(b) by 0 days.

(21) Appl. No.: 16/049,252

(22) Filed: Jul. 30, 2018

(65) Prior Publication Data

US 2018/0333518 A1 Nov. 22, 2018

Related U.S. Application Data

(60) Continuation of application No. 14/878,935, filed on Oct. 8, 2015, now Pat. No. 10,058,638, which is a division of application No. 13/504,012, filed as application No. PCT/EP2010/066459 on Oct. 29, 2010, now Pat. No. 9,186,438.

(30) Foreign Application Priority Data

Oct. 30, 2009 (EP) ..................................... 09174578

(51) Int. Cl.
*A61L 31/04* (2006.01)
*A61L 29/04* (2006.01)

(52) U.S. Cl.
CPC ........... *A61L 31/041* (2013.01); *A61L 29/049* (2013.01); *A61L 2400/10* (2013.01); *Y10T 428/139* (2015.01)

(58) Field of Classification Search
CPC .. A61L 31/041; A61L 29/049; A61L 2400/10; Y10T 428/139
See application file for complete search history.

*Primary Examiner* — Michael C Miggins
(74) *Attorney, Agent, or Firm* — Taft Stettinius & Hollister LLP; Ryan O. White

(57) ABSTRACT

The present invention relates to a medical tube article comprising a polymer mixture of a thermoplastic or thermocuring polymer base material and an amphiphilic block copolymer.

20 Claims, 4 Drawing Sheets

MEDICAL TUBE ARTICLE

CROSS-REFERENCE

This application is a continuation application of U.S. patent application Ser. No. 14/878,935, filed on Oct. 8, 2015 which is a divisional application of U.S. patent application Ser. No. 13/504,012, filed Apr. 25, 2012, now U.S. Pat. No. 9,186,438, which is a U.S. national stage of application No. PCT/EP2010/066459, filed on Oct. 29, 2010, which claims the benefit of European Application No. 09174578.6, filed on Oct. 30, 2009, all of which incorporated herein by reference in their entirety.

FIELD OF THE INVENTION

The present invention relates to a medical hollow tube article comprising a polymer mixture.

BACKGROUND ART

U.S. Pat. No. 5,084,315 discloses an article which becomes lubricious when wet, and which comprises a base polymer and a coating composition thereon. When using medical articles, for instance when inserting one article into another, scraping of the article surface might occur. This coated article has the drawback that it is possible to remove the coating from the surface of the article during such scraping of the surface, which causes the scraped area to be less lubricious.

Furthermore, when using a medical article, such as a tube in human orifices, some of the coating will always be left inside the person, which can be harmful and thus unacceptable.

SUMMARY OF THE INVENTION

It is an object of the present invention to wholly or partly overcome the above disadvantages and drawbacks of the prior art. More specifically, it is an object to provide an improved medical article which maintains a low friction property even when a surface is scraped. In this way, the lubricious properties are maintained throughout the entire surface of the article.

An additional object is to provide a product easy to manufacture while maintaining the mechanical properties of the product.

The above object, together with numerous other objects, advantages, and features, which will become evident from the below description, are accomplished by a solution in accordance with the present invention by a medical tube article moulded or extruded from a polymer mixture comprising a first and a second polymer, the first polymer being a thermoplastic or thermo-curing polymer and the second polymer being an amphiphilic block copolymer possessing both hydrophilic and lipophilic properties.

In one embodiment the amphiphilic block copolymer may be a hydrocarbon chain block of the formula $CH_3CH_2(CH_2CH_2)_a$ where "a" is 10, 11, 12, 13, 14, 15, 16, 17, 18, 19, 20, 21, 22, 23, 24 or 25, and a B-block, said B-block being hydrophilic.

Thus, a medical article is provided, comprising a thermoplastic polymer as a basis material and an amphiphilic block copolymer possessing both hydrophilic and lipophilic properties and comprising a main block being hydrophobic and another block being hydrophilic. The first polymer acts as a basis material and provides excellent mechanical properties, and since the hydrophilic block of the amphiphilic block copolymer seeks towards the surface of the article due to its incompatibility with the basis polymer, the friction efficiency of the surface is reduced. The hydrocarbon chain and the lipophilic and hydrophobic block of the amphiphilic block copolymer ensure that the hydrophilic part is secured to the basis material below and to the basis material as such. In this way, it is obtained that the properties of the surface remain intact regardless of which mechanical force the surface is exposed to, such as intentional scraping of the article surface.

The lipophilic property of the amphiphilic block copolymer ensures that the block copolymer is mixed with the first polymer and thus that the block copolymer is securely fastened to the first polymer. The hydrophobic block of the amphiphilic block copolymer is moreover compatible with hydrophobic parts of the first polymer acting as the basis polymer.

In a polymer mixture with a hydrophobic basis polymer, such as polyolefin, the hydrophilic part of the amphiphilic block copolymer will diffuse to the surface due to incompatibility with the hydrophobic first polymer.

Furthermore, it is obtained that the medical article can be sufficiently wetted just by wiping the surface with a wet tissue, since the hydrophilic part of the amphiphilic block copolymer diffuses to the surface forming a very thin layer, which thin layer requires less water than a thicker coating layer. By mixing the first polymer with an amphiphilic block copolymer, an article having an inherent lubricious property is obtained, and furthermore, the product is easily manufactured just by moulding or extruding the article and thus, no subsequent coating process is needed, which saves manufacturing costs and time.

In one embodiment, the thermoplastic first polymer may be selected from the group of: Polyolefin, Polyvinylchloride (PVC), polyurethane (PUR), Polyolefin, Styrene-butadiene copolymer (SBC), Styrene-ethylene-butylene-styrene copolymer (SEBS) and thermoplastic elastomers, or combinations thereof.

In another embodiment, the B-block may be a hydrophilic oligomer, i.e. a homo- or co-oligomer, consisting of between 2 and 10 monomer units derived from monomers selected from the group of: ethylene oxide, propylene oxide, ethylene glycol, propylene glycol, epichlorhydrin, acrylic acid, methacrylic acid, ethylene imine, caprolactone, vinyl alcohol and vinyl acetate.

Furthermore, the amphiphilic block copolymer may be either Irgasurf™, Aquazol™ or Unithox™.

In addition, the amphiphilic block copolymer may constitute 0.1-20% by weight, preferably 0.5-15% by weight and more preferably 0.5-5% by weight of the polymer mixture. The article may be any medical hollow tube article, such as an airway tube, a feeding catheter, an intestinal catheter a suction catheter or a urine catheter.

Additionally, the medical article has a surface friction, and the surface friction may be a kinetic coefficient of friction of less than 0.4, preferably in the closed interval 0.2-0.1.

In addition, the polymer mixture has a concentration of B-block, and the concentration of B-block at the surface of the article may be more than 2-60 times the concentration of B-block in the centre of the polymer mixture, preferably 3-50 times the concentration of B-block in the centre of the polymer mixture. Furthermore, the thermoplastic first polymer may be either Accurel™, Styroflex™, Styrolux™, MeliflleX™ or Mediprene™, which are all hydrophobic.

Also, the thermoplastic first polymer may be Estane™ 58315, which is both hydrophobic and hydrophilic.

The invention also relates to the use of a medical article as disclosed above for insertion into human orifices, such as airways, the rectum, the vagina or the urethra.

Finally, the invention relates to a method for manufacturing a medical tube article as disclosed above, comprising the steps of:
mixing a granulate blend of a first polymer being a thermoplastic or thermo-curing polymer and a second polymer being an amphiphilic copolymer, and
injection moulding or extrusion of the medical article.

In one embodiment of the method, the amphiphilic block copolymer may possess both hydrophilic and lipophilic properties.

Moreover, the method may further comprise the step of melting the granulate blend of the first polymer being the thermoplastic or thermo-curing polymer and the second polymer being the amphiphilic copolymer and forming another granulate, each granulate being a mixture of the first and the second polymer.

BRIEF DESCRIPTION OF THE DRAWINGS

The invention and its many advantages will be described in more detail below with reference to the accompanying schematic drawings, which for the purpose of illustration show some non-limiting embodiments and in which.

All the figures are highly schematic and not necessarily to scale, and they show only those parts which are necessary in order to elucidate the invention, other parts being omitted or merely suggested.

DETAILED DESCRIPTION OF THE INVENTION

Figure 1:
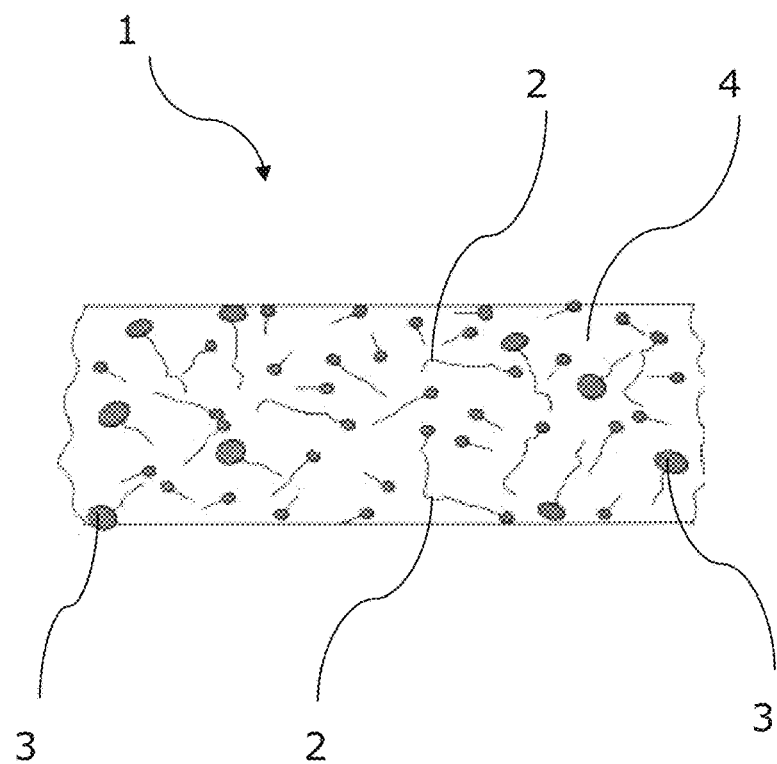
FIG. 1 shows a part of an article manufactured from a polymer mixture according to the invention, which is in molten state.

FIG. 1 shows a sample manufactured from a polymer mixture according to the invention, which sample is shown in its molten state. The polymer mixture comprises a second polymer being an amphiphilic copolymer 2, 3 which is mixed in a first polymer acting as a basis material 4. The basis material 4 is a thermoplastic or a thermocuring polymer. The amphiphilic block copolymer 2, 3 is a hydrocarbon chain block of the formula $CH_3CH_2(CH_2CH_2)_a$ where "a" is 10, 11, 12, 13, 14, 15, 16, 17, 18, 19, 20, 21, 22, 23, 24 or 25, and a hydrophilic B-block. The hydrophilic B-block is a hydrophilic oligomer, i.e. a homo- or co-oligomer, consisting of between 2 and 10 monomer units derived from monomers selected from the group of ethylene oxide, propylene oxide, ethylene glycol, propylene glycol, epichlorhydrin, acrylic acid, methacrylic acid, ethylene imine, caprolactone, vinyl alcohol and vinyl acetate. The thermoplastic basis material 4 may be selected from the group of Polyolefin, Polyvinylchloride (PVC), polyurethane (PUR), Polyolefin, Styrene-butadiene copolymer (SBC), Styrene-ethylene-butylene-styrene copolymer (SEBS) and thermoplastic elastomers, or a combination thereof. The sample is made of granulate comprising the first polymer 4 and the second polymer being the amphiphilic block copolymer 2, 3 in a suitable mixture and is delivered in granulate which, during a normal moulding or extrusion process, is heated and formed into the article in question.

Thus, the first and the second polymer are mixed to form one mixture comprising both hydrophilic and lipophilic properties. Subsequently, the mixture is moulded or extruded into a tube-shaped article. The first polymer acts as a basis material and provides excellent mechanical properties. The amphiphilic block copolymer possesses both hydrophilic and lipophilic properties and comprises a block which is hydrophobic and another block which is hydrophilic. The hydrophilic block of the amphiphilic block copolymer seeks towards the surface of the article due to its incompatibility with the basis polymer, the friction efficiency of the surface being reduced as a result. The hydrocarbon chain and the lipophilic and hydrophobic block of the amphiphilic block copolymer ensure that the hydrophilic block is secured in the basis material.

The first and the second polymer are comprised in the same compound so that each granulate comprises both the first and the second polymer before moulding or extrusion of the article. Moulding or extruding the article from one mixture of the first and second polymer eliminates the subsequent process of coating the article, and as the element resulting in the hydrophilic property on the surface of the article is anchored chemically in the basis polymer it is not easily wiped off or left inside the patient. Furthermore, if the surface for some reason should be scratched, new hydrophilic parts will diffuse to the surface of the article in order to restore the chemical state of equilibrium while still anchoring the hydrophobic and lipophilic part of the amphiphilic block copolymer in the basis material.

The lipophilic property of the amphiphilic block copolymer ensures that the block copolymer is mixed with the first polymer and thus that the block copolymer is securely fastened to the first polymer. Furthermore, the hydrophobic part of the amphiphilic block copolymer is compatible with the hydrophobic parts of the first polymer and therefore acts as a compatibiliser both when mixing the first and the second polymer in order to make the granulate and in the subsequent moulding or extrusion process.

In a hydrophobic basis polymer, such as polyolefin, SEBS-, SIS- and SBC-elastomers as a first polymer, the hydrophilic part of the amphiphilic block copolymer will diffuse to the surface due to incompatibility with the hydrophobic first polymer.

A further advantage is that the medical article can be sufficiently wetted just by wiping the surface with a wet tissue, or by high humidity or moisture, since the hydrophilic part of the amphiphilic block copolymer diffuses to the surface forming a very thin layer, which thin layer requires less water than a thicker coating layer.

Figure 2:
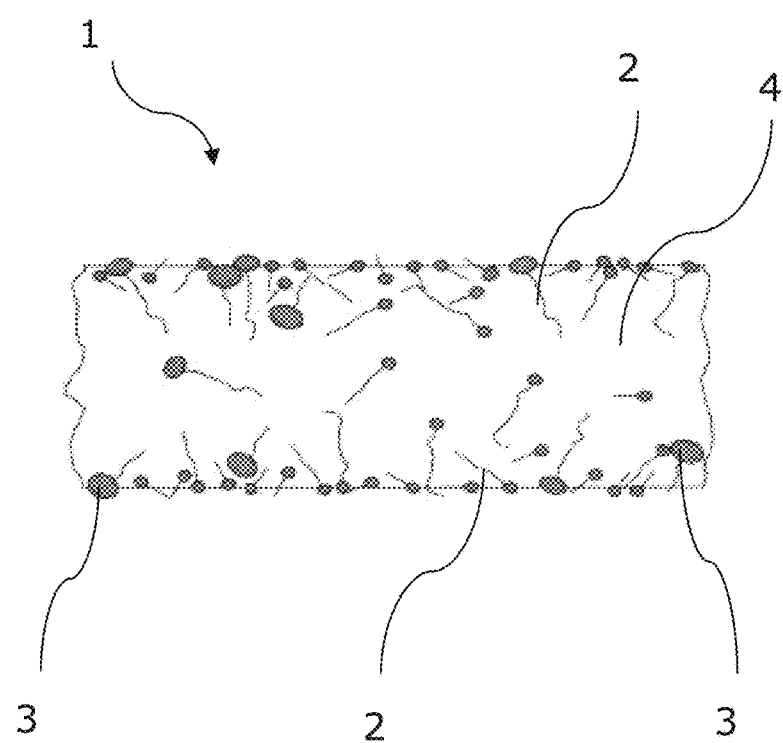
FIG. 2 shows a part of an article manufactured from a polymer mixture during cooling.

FIG. 2 shows how the material in the polymer reacts during cooling as the amphiphilic block copolymer 2, 3 places itself in the cooled material in such a way that the hydrophilic B-block seeks towards the surface, and the carbon chain block ensures that the B-block is retained in the basis material 4. The basis material 4 could be either Polyolefin, Polyvinylchloride (PVC), polyurethane (PUR), Polyolefin, Styrene-butadiene copolymer (SBC), thermoplastic elastomers or Styrene-ethylene-butylene-styrene copolymer (SEBS). In this way, the surface will not be able to change its mechanical properties, such as its lubricious property, when scraped, as a new state of equilibrium will be created at the surface in that the hydrophilic B-block seeks towards the surface. Compared to a coated surface which is scraped and looses part of its coating during the scraping process, an article manufactured from a material according to the invention does not change its mechanical properties as the hydrocarbon chain ensures that the amphiphilic block copolymer 2, 3 is safely secured to the base material 4.

By mixing the basis material 4 with an amphiphilic block copolymer, the article has both excellent mechanical properties and an inherent lubricious property since the hydrophilic block seeks towards the surface of the article due to its affinity to liquid. The hydrocarbon chain of amphiphilic block copolymer 2, 3 ensures that the hydrophilic part is secured in the base material 4. In this way, it is obtained that the properties of the surface remain intact regardless of which mechanical acts the surface is exposed to, such as intentional scraping of the article surface.

Furthermore, by mixing the base material 4 with an amphiphilic block copolymer 2, 3 so that the article has an inherent lubricious property, no subsequent coating process is needed, which saves manufacturing costs and time.

The amphiphilic block copolymer 2, 3 could be either Irgasurf™ or Unithox™, which are both commercially available copolymers. The weight of the amphiphilic block copolymer 2, 3 compared to the weight of the entire polymer mixture is preferably between 0.1%-20%, more preferably 0.5%-15% and even more preferably 0.5%-5%.

Due to the small amount of amphiphilic block copolymer, the mechanical properties of the basis material, i.e. the first polymer, are not substantially decreased and the mechanical properties of the medical article are thus maintained.

The thermoplastic base material 4 could for instance be Accurel™, Styroflex™, Styrolux™ Mediprene™, Meliflex™ or Estane™, which are all thermoplastic polymers commercially available. The material could be used for producing a medical article such as airway tubes of different kinds, for instance tracheal tubes or laryngeal masks, or urine catheters.

Figure 3:
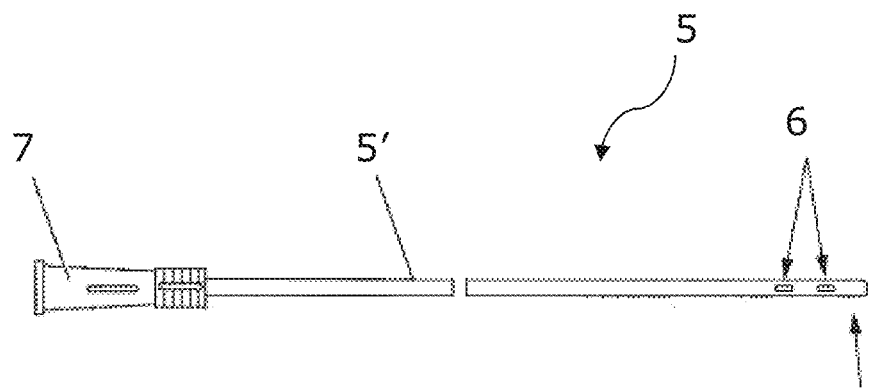
FIG. 3 shows a first example of a medical article manufactured from a material according to the invention.

FIG. 3 shows an example of an airway tube, such as a suction catheter 5 comprising a hollow tube part 5' which is manufactured from a material according to the invention. The catheter may have openings 6 in the distal end, and in the proximal end, the catheter may be provided with a connector 7 for gripping the tube part 5'. It is an advantage when using the catheter that the surface becomes very slippery when wetted only slightly with body fluids before being placed in the orifice. Whereas the coated articles known from the prior art have to be submerged in water for up to 30 seconds in order to become sufficiently lubricous, the article of the present invention only needs to be wetted, e.g. by means of a wet tissue wiped over the surface, in order to become so.

Figure 4:
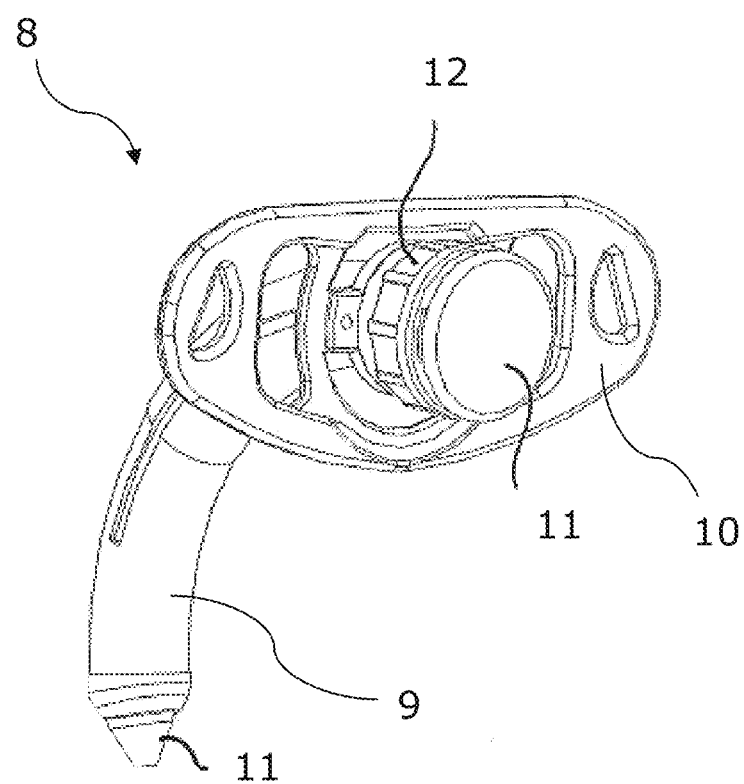
FIG. 4 shows a second example of a medical article where the article is an airway tube and is manufactured from a material according to the invention.

Furthermore, as the product of the present invention does not contain coatings as in prior art articles, substantially no chemical elements are left in the body. It is also an advantage that when the catheter has been removed from the body, there is no coating at the surface because the coating often drips and causes staining when in contact with body fluids. This is not the case when using a catheter according to the invention where no coating is used. An example of such a catheter is shown in WO 2008/155145 which is incorporated by reference. FIG. 4 shows an example of an airway tube, a tracheal stoma tube, where the tube part 9 can also advantageously be manufactured from a mixture according to the invention. This article comprises the tube part 9 itself, being the outer cannula, which should be slippery when entered into the airways. Inside the outer cannula an inner cannula 11 is placed, which can advantageously be manufactured from a polymer mixture according to the invention. The catheter is at the proximal end fastened to a flange 10, and a swivel locking member 12 is fastened to the outer cannula. A detailed description of this device is found in WO 2008/046418 which is incorporated by reference.

In another embodiment, the medical article is co-extruded having an outer layer of the mixture according to the present invention and an inner layer of a cheaper material or a material having different properties, such as an anti-bacterial property, e.g. comprising Ag ions.

In the example below, a method of determining the surface wear resistance compared to the surfaces of known coated articles is explained.

EXAMPLE

Measurements of the friction on round surfaces manufactured from a polymer mixture material according to the invention, i.e. on a catheter, are conducted.

Objective

The equipment is to be used to measure kinetic friction on round surfaces, for instance on tubes and rods at a predetermined distance. The test is only to be used for comparison between two articles, which requires the test articles to be of substantially the same dimensions.

Method

The friction will be calculated by using the Formula: $F=Fn*\mu$, where F(N) and Fn are recorded.

Fn is the weight of the round article, i.e. the tubing, including the fastening elements (called a fixture hereinafter)—Fx—multiplied by the gravitation. F is recorded by pulling the fixture in a horizontal direction.

The test equipment consists of:
a vertical tensile strength test machine (load cell 10 N),
a horizontal plane with a replaceable surface and a pulley for transforming the horizontal movement into a vertical movement, and
a slider-fixture for mounting of two tubings/rods. The weight of the slider-fixture can be adjusted.

Test Machine Used

Lloyd LRX PLUS, Ser. No. 105239, Load cell 10 N, Ser. No. 015511, Calibrated in June 2009.

Process

Figure 5:
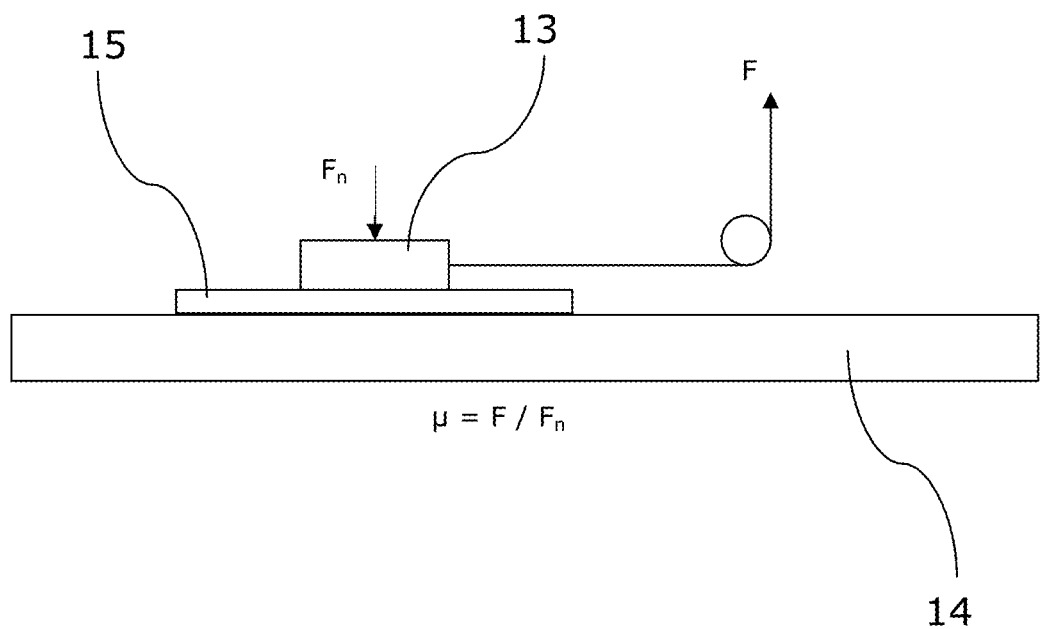
FIG. 5 shows an apparatus for testing the friction of the surface of an article manufactured from a material according to the invention.

With reference to FIG. 5, the test items 15 are mounted underneath the slider 13, and the replaceable surface is prepared. Currently, a wet wash leather is used. The slider 13 is placed on the replaceable surface and is made of two tubes manufactured from different materials, and the test sequence is started. The tube is placed on a plane surface 14 on which the wet wash leather is arranged.

The pulling force is recorded in a graph.

By the known factors F and Fn the Friction coefficient is calculated.

Recordings:
  Weight of slider
  Average force registered (1000 measure point/second within a defined part of movement)
  Pull speed (stationary value)
  Surface used
  Product tested, with available data of origins.

In table 1 the results of the experiments are listed.

The chosen material covers four samples manufactured from a material according to the invention. This is to be compared to four commercially available catheters: Speedi-Cath™, EasiCath™, LoFric™ and LoFric Plus™. All these commercially available catheters are coated. As can be seen from the results, the friction Fn measured on round items manufactured from a material according to the invention is much lower than the commercial catheters and is comparable with LoFric Plus™.

mixture are thus still maintained while at the same time providing the article with sufficient lubricious properties to be acceptable for a patient.

TABLE 2

| Code | Material | Kinetic Coefficient of Friction |
|---|---|---|
| F | Accurel ™ XP850 (97%) and Irgasurf ™ HL560 (3%) | 0.165 |
| H | Meliflex ™ M6504) (97%) and Irgasurf ™ HL560 (3%) | 0.186 |
| L | Estane ™ 58315 (PUR) (97%) and Irgasurf ™ HL560 (3%) | 0.155 |
| N | Mediprene ™ 500803M (polyolefin compound) (97%) and Irgasurf ™ HL560 (3%) | 0.1394 |
| O | Mediprene ™ OF500M (polyolefin compound) (97%) and Irgasurf ™ HL560 (3%) | 0.1594 |
| R | Mediprene ™ 500803M (polyolefin compound, | 0.2571 |

TABLE 1

| Code | F | FF | H | HH | EasiCath ™ | Speedi Cath ™ | LoFric ™ Nelaton | LoFric Plus ™ Nelaton |
|---|---|---|---|---|---|---|---|---|
| Weight of Slider $F_x$ [grams] | 317.5 | 317.5 | 317.5 | 317.5 | 317.5 | 317.5 | 317.5 | 317.5 | 317.5 | 317.5 |
| Wet wash leather | 4 B | 4 B | 4 B | 4 B | 4 B | 4 B | 4 B | 4 B | 4 B | 4 B |
| Pull velocity [mm/min] | 250 | 250 | 250 | 250 | 250 | 250 | 250 | 250 | 250 | 250 |
| Pull distance [mm] | 100 | 100 | 100 | 100 | 100 | 100 | 100 | 100 | 100 | 100 |
| Basis material | 100% Accurel ™ XP850 | 97% Accurel ™ XP850 | 85% Accurel ™ XP850 | 100% Meliflex ™ 6504 | 97% PP Meliflex ™ M6504 | 85% PP Meliflex ™ M6504 | — | — | — | — |
| Amphiphilic block co-polymer | 0% | 3% Irgasurf ™ 560 HL | 15% Irgasurf ™ 560 HL | 0% | 3% Irgasurf ™ 560 HL | 15% Irgasurf ™ 560 HL | — | — | — | — |
| Numbers of experiments | 8 | 8 | 8 | 8 | 8 | 8 | 8 | 8 | 8 | 8 |
| Friction of coefficient μ average | 1.452 | 0.1656 | 0.1182 | 1.3212 | 0.1861 | 0.1406 | 0.2072 | 0.3760 | 0.2401 | 0.1441 |
| Standard deviation of μ | 0.0763 | 0.0107 | 0.0045 | 0.0241 | 0.0296 | 0.0091 | 0.0086 | 0.0225 | 0.0086 | 0.0287 |

As can be seen from the results, the coefficient of the friction is reduced by nearly a factor 10 when 3% by weight Irgasurf™ is mixed in the basis material.

Figure 6:
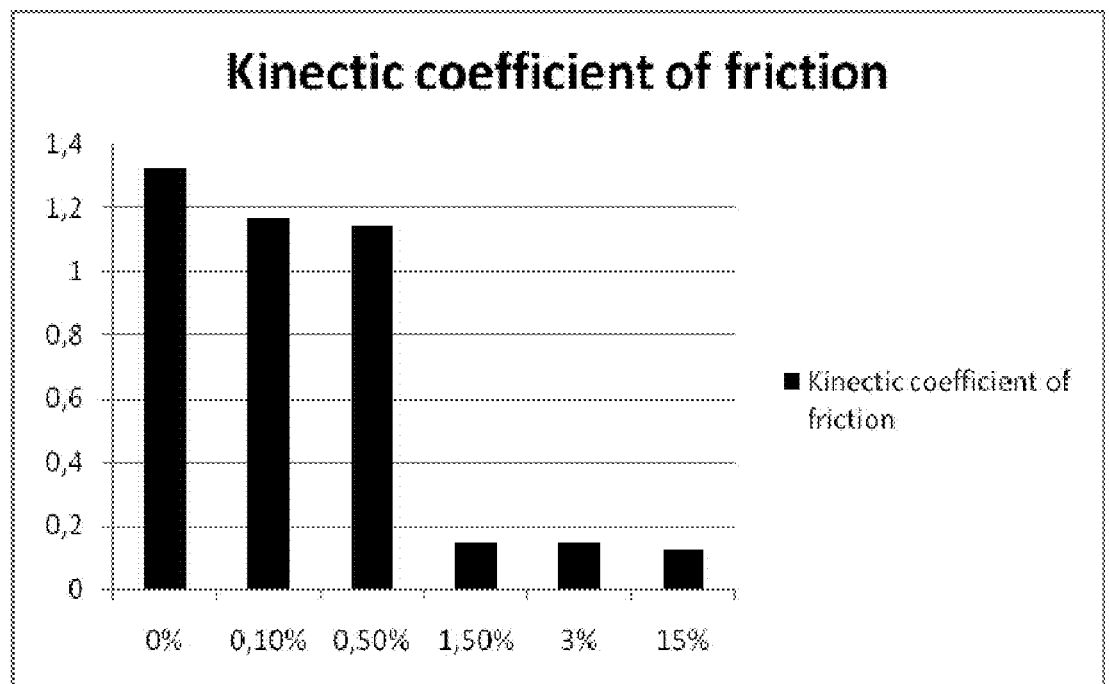
FIG. 6 shows a chart of different amounts of Irgasurf™ 560 HL in the basis material.

In FIG. 6, a chart is shown based on the measured kinetic coefficient of friction in articles of Meliflex™ M6504 mixed with 0.0%, 0.1%, 0.5%, 1.5%, 3.0 or 15% Irgasurf™ 560 HL. The kinetic coefficient of friction is measured to 1.32 at 0.0% Irgasurf™ 560 HL in the basis material Meliflex™ M6504, to 1.17 at 0.1% Irgasurf™ 560 HL, to 1.14 at 0.5% Irgasurf™ 560 HL, to 0.15 at 1.5% Irgasurf™ 560 HL, to 0.15 at 3% Irgasurf™ 560 HL, and to 0.13 at 15% Irgasurf™ 560 HL.

As can be seen from these results, the intended effect is obtained at 1.5% Irgasurf™ 560 HL mixed in Meliflex™ M6504, since the measured kinetic coefficient of friction is substantially reduced at this concentration, i.e. from 1.15 to 0.14, while the amount of Irgasurf™ 560 HL added is still very small, i.e. only 1.5%. The 5 mechanical properties of an article, such as a catheter, moulded or extruded from this TABLE 2-continued

| Code | Material | Kinetic Coefficient of Friction |
|---|---|---|
|  | shore hardness 80) (97%) and Irgasurf ™ HL560 (3%) |  |
| S | Mediprene ™ 500803M (polyolefin compound, shore hardness 85) (97%) and Irgasurf ™ HL560 (3%) | 0.2134 |
| T | Mediprene ™ 500803M (polyolefin compound, shore hardness 90) (97%) and Irgasurf ™ HL560 (3%) | 0.1941 |

Figure 7:
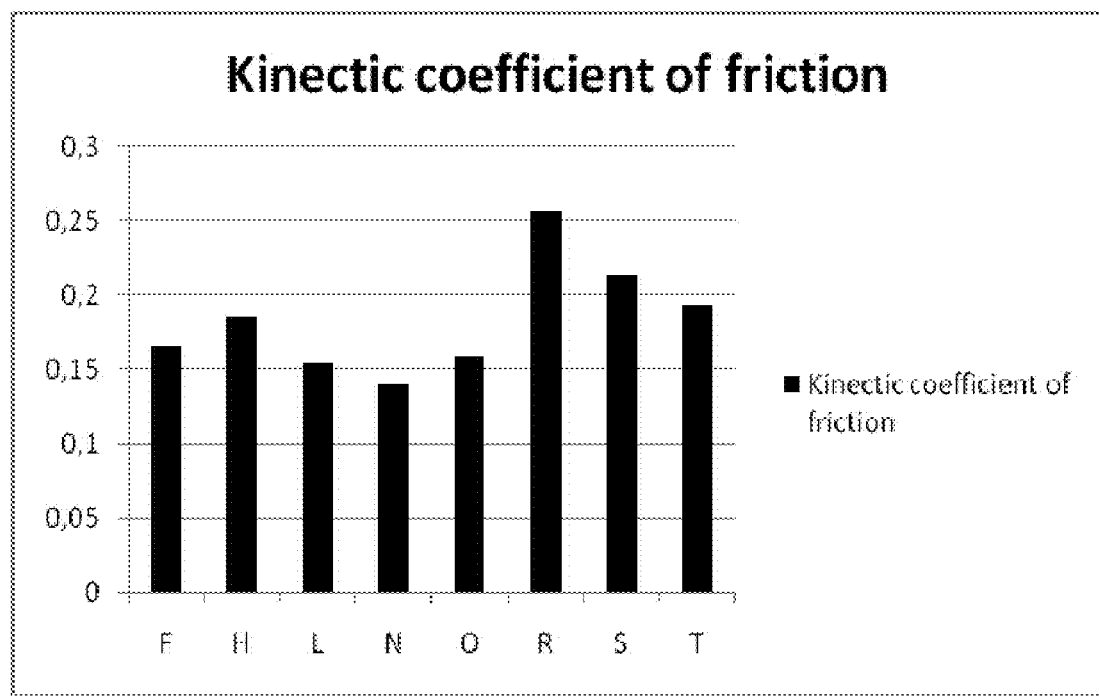
FIG. 7 shows a chart of different basis polymers comprising an amphiphilic block copolymer.

As can be seen from table 2, other thermoplastic polymers than Meliflex™ and Accurel™ can be used as the first polymer, i.e. the basis polymer. In table 2, the kinetic coefficients of friction at various basis polymers are listed and a chart from the results can be seen in FIG. 7. When comparing a tube article of a basis 5 material without any amphiphilic block copolymer in table 1, such as a tube article of 100% Accurel™ XP850, with the tube articles containing an amphiphilic block copolymer, the tube articles with amphiphilic block copolymer have a substantially lower kinetic coefficient of friction than those without amphiphilic block copolymer. As can be seen from table 2, Mediprene™ and Estane™ have also 0 proven to be suitable as a first polymer in order to reduce the surface friction of an article.

The surface of an article may refer to the outer surface and/or the inner surface of the article. Even though only the outer surface has been disclosed in the 5 above, an inner surface having a low kinetic coefficient of friction may be desirable as well, e.g. in medical tubes to be penetrated by instruments during examination of a patient.

The articles of the invention may be manufactured by extruding the article or by injection moulding.

Although the invention has been described in the above in connection with preferred embodiments of the invention, it will be evident for a person skilled in the art that several modifications are conceivable without departing from the invention as defined by the following claims.

1. Part of an article comprising a polymer according to the invention
2. Part of an amphiphilic block copolymer hydrocarbon chain block
3. The other part of the amphiphilic block copolymer, i.e. B-block
4. Thermoplastic or thermo curing polymer being the base material
5. Urine catheter comprising a hollow flexible tube
5' Hollow tube part
6. Openings
7. Connector
8. Airway tube (tracheal stoma tube)
9. Outer cannula
10. Flange for fastening the airway device
11. Inner cannula
12. Swivel locking member
13. Slider
14. Plane surface
15. Test item

What is claimed is:

1. A medical tube article molded or extruded from a polymer mixture comprising a first polymer and a second polymer: the first polymer being a thermoplastic or thermo-curing polymer, and the second polymer being an amphiphilic block copolymer possessing both hydrophilic and lipophilic properties, the amphiphilic block copolymer comprising a hydrophilic B-block, wherein a concentration of the hydrophilic B-block of the amphiphilic block copolymer at the surface of the article is more than 2-60 times a concentration of the hydrophilic B-block in the center of the polymer mixture.

2. The medical tube article according to claim 1, wherein said amphiphilic block copolymer is a hydrocarbon chain block of the formula $CH_3CH_2(CH_2CH_2)_a$ where "a" is 10, 11, 12, 13, 14, 15, 16, 17, 18, 19, 20, 21, 22, 23, 24 or 25, and the hydrophilic B-block.

3. The medical tube article according to claim 1 wherein the amphiphilic block copolymer constitutes 0.5-15% by weight of the polymer mixture.

4. The medical tube article according to claim 1, wherein the amphiphilic block copolymer constitutes 0.5-5% by weight of the polymer mixture.

5. The medical tube article according to claim 1, wherein the medical tube article is an airway tube, a feeding catheter, an intestinal catheter, a suction catheter or a urine catheter.

6. The medical tube article according to claim 1, wherein the medical tube article has a surface friction, and the surface friction is less than 0.4.

7. The medical tube article according to claim 1, wherein the medical tube article has a surface wear resistance, and the surface wear resistance compared to the surface of coated articles is in the interval 1.5:1-100:1.

8. The medical tube article according to claim 1, wherein the first polymer is selected from the group of: polyolefin, polyvinylchloride (PVC), polyurethane (PUR), styrene-butadiene copolymer (SBC), styrene-ethylene-butylene-styrene copolymer (SEBS) and thermoplastic elastomers, or combinations thereof.

9. The medical tube article according to claim 8, wherein the B-block is a hydrophilic oligomer, i.e. a homo- or co-oligomer, consisting of between 2 and 10 monomer units derived from monomers selected from the group of ethylene oxide, propylene oxide, ethylene glycol, propylene glycol, epichlorhydrin, acrylic acid, methacrylic acid, ethylene imine, caprolactone, vinyl alcohol and vinyl acetate.

10. A medical tube article comprising:
a center, wherein the center is formed from a polymer mixture including a first polymer and an amphiphilic block copolymer having a hydrophilic B-block, and wherein the medical tube article has a first concentration of the hydrophilic B-block of the amphiphilic block copolymer at the center; and
a surface outwardly spaced from the center, wherein the surface is formed from the polymer mixture, and wherein the medical tube article has a second concentration of the hydrophilic B-block of the amphiphilic block copolymer at the surface that is at least two times greater than the first concentration at the center.

11. The medical tube article of claim 10, wherein:
the first polymer is selected from the group of polyolefin, polyvinylchloride (PVC), polyurethane (PUR), styrene-butadiene copolymer (SBC), styrene-ethylene-butylene-styrene copolymer (SEBS), and thermoplastic elastomers, or combinations thereof; and
the B-block is a hydrophilic oligomer, i.e. a homo- or co-oligomer, consisting of between 2 and 10 monomer units derived from monomers selected from the group of ethylene oxide, propylene oxide, ethylene glycol, propylene glycol, epichlorhydrin, acrylic acid, methacrylic acid, ethylene imine, caprolactone, vinyl alcohol, and vinyl acetate.

12. The medical tube article of claim 10, wherein the second concentration at the surface is at least 2-60 times greater than the first concentration at the center.

13. The medical tube article of claim 10, wherein the amphiphilic block copolymer constitutes 0.5-5% by weight of the polymer mixture.

14. The medical tube article of claim 10, wherein a surface friction of the medical tube article is less than 0.4.

15. The medical tube article of claim 10, wherein the amphiphilic block copolymer is a hydrocarbon chain block of the formula $CH_3CH_2(CH_2CH_2)_a$ where "a" is 10, 11, 12, 13, 14, 15, 16, 17, 18, 19, 20, 21, 22, 23, 24 or 25, and the hydrophilic B-block.

16. A medical tube article comprising:
a center, wherein the center is formed from a polymer mixture including a first polymer and an amphiphilic block copolymer having a hydrophilic B-block, and wherein the medical tube article has a first concentration of the hydrophilic B-block of the amphiphilic block copolymer at the center; and a surface outwardly spaced from the center, wherein the surface is formed from the polymer mixture, and wherein the medical tube article has a second concentration of the hydrophilic B-block of the amphiphilic block copolymer at the surface that is at least two times greater than the first concentration at the center, wherein a surface friction of the medical tube article is less than 0.4.

17. The medical tube article of claim 16, wherein:

the first polymer is selected from the group of polyolefin, polyvinylchloride (PVC), polyurethane (PUR), styrene-butadiene copolymer (SBC), styrene-ethylene-butylene-styrene copolymer (SEBS), and thermoplastic elastomers, or combinations thereof; and the B-block is a hydrophilic oligomer, i.e. a homo- or co-oligomer, consisting of between 2 and 10 monomer units derived from monomers selected from the group of ethylene oxide, propylene oxide, ethylene glycol, propylene glycol, epichlorhydrin, acrylic acid, methacrylic acid, ethylene imine, caprolactone, vinyl alcohol, and vinyl acetate.

18. The medical tube article of claim 16, wherein the second concentration at the surface is at least 2-60 times greater than the first concentration at the center.

19. The medical tube article of claim 16, wherein the amphiphilic block copolymer is a hydrocarbon chain block of the formula $CH_3CH_2(CH_2CH_2)_a$ where "a" is 10, 11, 12, 13, 14, 15, 16, 17, 18, 19, 20, 21, 22, 23, 24 or 25, and the hydrophilic B-block.

20. The medical tube article of claim 16, wherein the amphiphilic block copolymer constitutes 0.5-5% by weight of the polymer mixture.

* * * * *